United States Patent
Li

(10) Patent No.: US 8,728,169 B2
(45) Date of Patent: May 20, 2014

(54) MEDICAL APPARATUSES FOR DELIVERY OF UROLOGICALLY BENEFICIAL AGENTS

(75) Inventor: Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 35 days.

(21) Appl. No.: 13/468,575

(22) Filed: May 10, 2012

(65) Prior Publication Data

US 2012/0290100 A1  Nov. 15, 2012

Related U.S. Application Data

(60) Provisional application No. 61/484,773, filed on May 11, 2011.

(51) Int. Cl.
   *A61F 2/04* (2013.01)

(52) U.S. Cl.
   USPC .................................................. 623/23.65

(58) Field of Classification Search
   USPC ............... 623/23.65–23.68; 604/151, 257
   See application file for complete search history.

(56) References Cited

U.S. PATENT DOCUMENTS

| | | | |
|---|---|---|---|
| 6,524,268 B2 * | 2/2003 | Hayner et al. | 604/8 |
| 8,308,710 B2 * | 11/2012 | Landman et al. | 604/523 |
| 2004/0225372 A1 * | 11/2004 | Gellman et al. | 623/23.66 |
| 2005/0055104 A1 * | 3/2005 | Arnal et al. | 623/23.66 |
| 2005/0107736 A1 | 5/2005 | Landman et al. | |
| 2008/0234659 A1 | 9/2008 | Cheng et al. | |
| 2009/0171465 A1 | 7/2009 | Bucay-Couto et al. | |
| 2009/0187254 A1 | 7/2009 | Deal et al. | |
| 2009/0248169 A1 | 10/2009 | Li | |
| 2009/0281635 A1 | 11/2009 | Li et al. | |
| 2010/0160848 A1 | 6/2010 | Ostrovsky et al. | |
| 2013/0123756 A1 * | 5/2013 | Eberli et al. | 604/544 |

FOREIGN PATENT DOCUMENTS

WO  2009029744 A1  3/2009

\* cited by examiner

*Primary Examiner* — Suzette J Gherbi
(74) *Attorney, Agent, or Firm* — Kacvinsky Daisak Bluni PLLC

(57) ABSTRACT

The present invention provides implantable or insertable medical apparatuses that deliver one or more urologically beneficial agents to the urinary tract. In one aspect, the medical apparatuses comprise a reservoir, a catheter, an implantable or insertable urological medical device, and an optional pump.

19 Claims, 5 Drawing Sheets

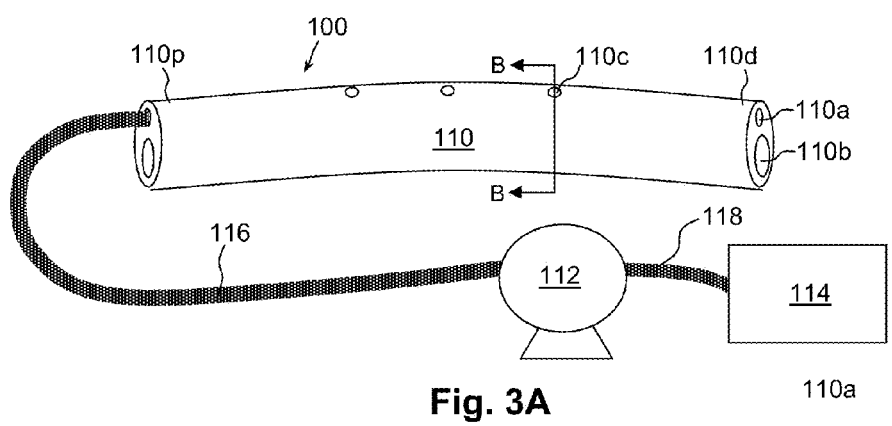
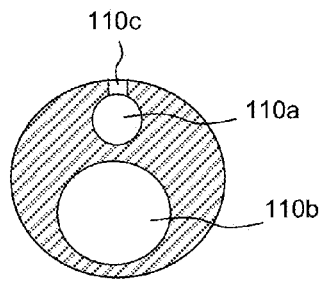 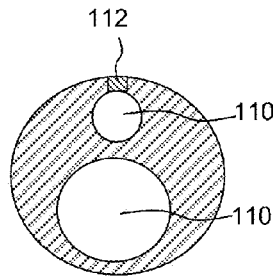 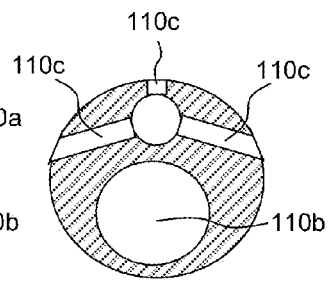
Fig. 3A
Fig. 3B    Fig. 3C    Fig. 3D

MEDICAL APPARATUSES FOR DELIVERY OF UROLOGICALLY BENEFICIAL AGENTS

STATEMENT OF RELATED APPLICATION

This application claims the benefit of U.S. Ser. No. 61/484,773, filed May 11, 2011 and entitled "MEDICAL APPARATUSES FOR DELIVERY OF UROLOGICALLY BENEFICIAL AGENTS," which is hereby incorporated by reference in its entirety.

BACKGROUND OF THE INVENTION

Various urological medical devices have been developed for implantation or insertion into patients. As an example, polymeric ureteral stents are widely used to facilitate drainage in the upper urinary tract (e.g., drainage from the kidney to the bladder). They are used, for example, in post endourological procedures to act as a scaffold in the event of ureteral obstruction secondary to the procedure. Ureteral stents are also used as palliative devices to provide patency in the presence of congenital defects, strictures or malignancies, as well as in other instances where ureteral obstruction may occur. A schematic illustration of a ureteral stent 10 in accordance with the prior art is illustrated in FIGS. 1A and 1B. The stent 10 has a proximal (bladder) end 10p and a distal (renal) end 10d. It is a tubular polymeric extrusion having a shaft 12, a distal renal retention structure (e.g., renal coil or "pigtail" 14), and a proximal retention structure (e.g., bladder coil or "pigtail" 16). These retention structures prevent upward migration of the stent toward the kidney or downward migration of the stent toward the bladder. The shaft 12 in cross-section is a single extruded layer as seen from FIG. 1B, which is taken along line b-b of FIG. 1A. Once properly deployed in the ureter, the stent 10 provides ureteral rigidity and allows the passage of urine. The stent 10 of FIGS. 1A and 1B is further provided with the following features: (a) a tapered tip 11, to aid insertion, (b) a central lumen 10c, (c) multiple side ports 18 (one numbered), which are arranged in a spiral pattern down the length of the body to promote drainage, (d) graduation marks 25 (one illustrated) for visualization by the physician to know when the appropriate length of stent has been inserted into the ureter, and (e) a suture 22, which aids in positioning and withdrawal of the stent. During placement, such ureteral stents 10 are typically placed over a urology guide wire, through a cystoscope and advanced into position. Once the distal end of the stent is advanced into the kidney/renal calyx, the guide wire is removed, allowing the coils 14, 16 to form in the kidney 19 and bladder 20, as shown in FIG. 2. As shown in FIG. 2, the stent 10 extends through the ureteral orifice 21a and into the bladder 20. For clarity, the ureter entering bladder 20 through the opposite ureteral orifice 21b is not shown.

SUMMARY OF THE INVENTION

The present invention provides implantable or insertable medical apparatuses that deliver one or more urologically beneficial agents to the urinary tract. In one aspect, the medical apparatuses comprise a reservoir, a catheter, an implantable or insertable urological medical device, and an optional pump.

Advantages of the present invention include the fact that medical apparatuses may be provided which locally deliver urologically beneficial agents, thereby avoiding the need for systemic drug administration, which typically requires higher quantities of drug to be efficacious and may have higher side effects.

Another advantage of the present invention is that medical apparatuses may be provided, which act as a delivery platform for essentially any urologically beneficial agent a physician or other caregiver may wish to administer.

Yet another advantage of the present invention is that medical apparatuses may be provided which can locally deliver an essentially limitless supply of one or more urologically beneficial agents to a subject.

These and other aspects, embodiments and advantages of the present invention will become immediately apparent to those of ordinary skill in the art upon review of the Detailed Description and any claims to follow.

BRIEF DESCRIPTION OF THE DRAWINGS

FIG. 3A is a schematic illustration of a medical device in accordance with an embodiment of the invention. FIG. 3B is a cross-section of the medical device of FIG. 3A, taken along plane B-B. FIGS. 3C and 3D are alternative cross-sections to FIG. 3B.

DETAILED DESCRIPTION OF THE INVENTION

Figure 1A:
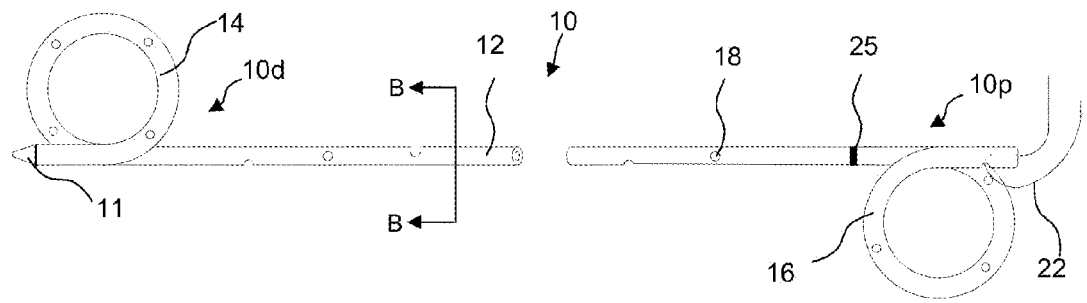
FIG. 1A is a schematic representation of a ureteral stent, according to the prior art.
Figure 1B:
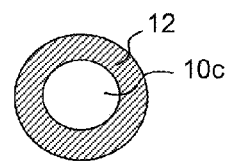
FIG. 1B is a cross-section taken along plane A-A of FIG. 1A.
Figure 2:
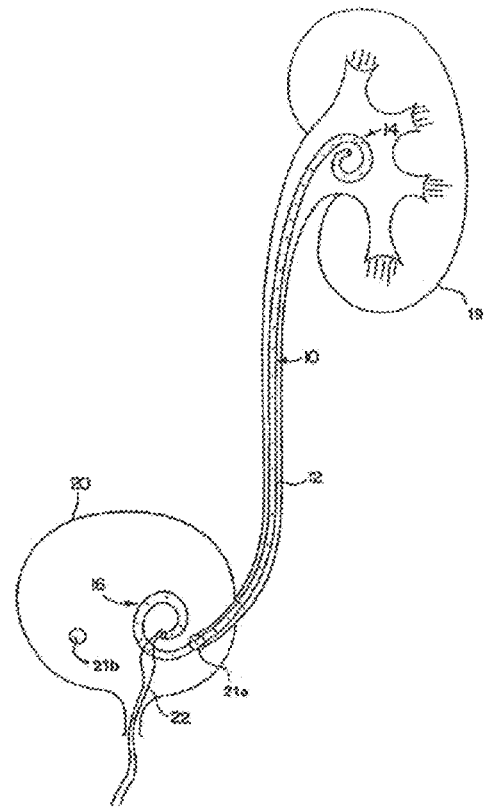
FIG. 2 shows a ureteral stent like that of FIG. 1A as positioned within the body.

A more complete understanding of the present invention is available by reference to the following detailed description of numerous aspects and embodiments of the invention. The detailed description of the invention which follows is intended to illustrate but not limit the invention.

The present invention provides implantable or insertable medical apparatuses that deliver one or more urologically beneficial agents into the urinary tract.

In one aspect, the invention provides medical apparatuses by which urologically beneficial agents are delivered to the urinary tract of a subject. The medical apparatuses comprise a reservoir, a catheter, an implantable or insertable urological medical device, and an optional pump.

For example, as discussed in more detail below, in certain embodiments, medical apparatuses are provided, which comprise: (a) an external reservoir that is configured to remain external to the urinary tract of a subject, (b) an insertable catheter having proximal (external) and distal (internal) ends that is configured to be inserted into the urinary tract, the catheter having a catheter lumen that extends from the proximal end to the distal end of the catheter, and (c) a urological medical device that is configured to be implanted in the urinary tract (e.g., a ureteral stent or prostate stent or a urethral catheter), the urological medical device having an agent delivery lumen that extends from the proximal end of the urological medical device into the urological medical device. The interior of the external reservoir is in fluid communication with the proximal end of the catheter lumen, and the distal end of the catheter lumen is in fluid communication with the proximal end of the agent delivery lumen. Moreover, the medical apparatus is adapted to deliver a urologically beneficial agent from the reservoir, through the catheter, and into the agent delivery lumen of the urological medical device. In certain embodiments (e.g., where the apparatuses are not configured to deliver the urologically beneficial agents by gravity feed), the medical apparatus further comprises a pump for pumping the urologically beneficial agent.

Preferred subjects (also referred to as "patients") are vertebrate subjects, more preferably mammalian subjects, including human subjects, pets and livestock.

As used herein, "proximal end" refers to the end of the object that lies closest to or outside the urethral exit (downstream) in the urinary tract, and "distal end" refers to the end of an implanted or inserted object that lies furthest from the urethral exit (upstream) in the urinary tract.

In some embodiments, devices are provided which are adapted to be advanced over a guide wire and/or advanced through a channel, for example, a channel associated with a guide catheter or scope.

In some embodiments, devices may be employed that take on a particular beneficial shape in vivo, for example, upon removal of a guide wire or upon emergence from a channel (e.g., due to elastic rebound of the material) or upon application of an external stimulus such as heat or light (e.g., where a shape memory material such as a shape memory polymer is employed). For example, the device may comprise one or more retention elements which take on a non-linear form such as a coiled configuration. Such constructions allow the medical device to be held in place in the urinary tract, for example, by forming a coil or other retention element in the kidney (e.g., in the renal calyx and/or renal pelvis), the bladder, or both.

Urologically beneficial agents for use in the medical devices of the invention include antimicrobial agents, agents that reduce pain and/or discomfort (also referred herein as "discomfort reducing agents"), anti-cancer drugs, and combinations thereof.

The term "antimicrobial agent" as used herein means a substance that kills microbes and/or inhibits the proliferation and/or growth of microbes, particularly bacteria, fungi and yeast. Antimicrobial agents, therefore, include biocidal agents and biostatic agents as well as agents that possess both biocidal and biostatic properties. In the context of the present disclosure, the antimicrobial agent kills microbes and/or inhibits the proliferation and/or growth of microbes on and around the surfaces of the implanted or inserted urological medical device, and can therefore inhibit biofilm formation (encrustation) in some cases.

Antimicrobial agents may be selected, for example, from triclosan, chlorhexidine, nitrofurazone, benzalkonium chlorides, silver salts and antibiotics, such as rifampin, gentamicin and minocycline, hyaluronic acid and combinations thereof, among others.

Further antimicrobial agents may be selected, for example, from suitable antibiotic agents selected from the following: the penicillins (e.g., penicillin G, methicillin, oxacillin, ampicillin, amoxicillin, ticarcillin, etc.), the cephalosporins (e.g., cephalothin, cefazolin, cefoxitin, cefotaxime, cefaclor, cefoperazone, cefixime, ceftriaxone, cefuroxime, etc.), the carbapenems (e.g., imipenem, metropenem, etc.), the monobactems (e.g., aztreonem, etc.), the carbacephems (e.g., lora-carbef, etc.), the glycopeptides (e.g., vancomycin, teichoplanin, etc.), bacitracin, polymyxins, colistins, fluoroquinolones (e.g., norfloxacin, lomefloxacin, fleroxacin, ciprofloxacin, enoxacin, trovafloxacin, gatifloxacin, etc.), sulfonamides (e.g., sulfamethoxazole, sulfanilamide, etc.), diaminopyrimidines (e.g., trimethoprim, etc.), rifampin, aminoglycosides (e.g., streptomycin, neomycin, netilmicin, tobramycin, gentamicin, amikacin, etc.), tetracyclines (e.g., tetracycline, doxycycline, demeclocycline, minocycline, etc.), spectinomycin, macrolides (e.g., erythromycin, azithromycin, clarithromycin, dirithromycin, troleandomycin, etc.), and oxazolidinones (e.g., linezolid, etc.), among others, as well as combinations and pharmaceutically acceptable salts, esters and other derivatives of the same.

Discomfort reducing agents include antispasmodic agents, ketorolac, corticosteroids, narcotic analgesic agents, non-narcotic analgesic agents, local anesthetic agents, and combinations thereof.

Antispasmodic agents may be selected, for example, from suitable members of the following: alpha-adrenergic blockers, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenyl-propylamine, tropenzile, trospium chloride, and xenytropium bromide, among others, as well as combinations and pharmaceutically acceptable salts, esters and other derivatives of the same.

Examples of alpha-adrenergic blockers for use in the present invention may be selected from suitable members of the following: alfuzosin, amosulalol, arotinilol, dapiprazole, doxazosin, ergoloid mesylates, fenspiride, idazoxan, indoramin, labetalol, manotepil, naftopidil, nicergoline, prazosin, tamsulosin, terazosin, tolazoline, trimazosin, and yohimbine, among others, as well as combinations and pharmaceutically acceptable salts, esters and other derivatives of the same. Of these, tamsulosin, alfuzosin, doxazosin, prazosin, tamsulosin and terazosin are alpha-1-adrenergic blockers, of which tamsulosin and alfuzosin are selective alpha-1-adrenergic blockers.

Examples of corticosteroids for use in the present invention may be selected from suitable members of the following: betamethasone, cortisone, dexamethasone, deflazacort, hydrocortisone, methylprednisolone, prednisolone, prednisone and triamcinolone, among others, as well as combinations and pharmaceutically acceptable salts, esters and other derivatives of the same.

Examples of narcotic analgesic agents for use in the present invention may be selected from suitable members of the following: codeine, morphine, fentanyl, meperidine, propoxyphene, levorphanol, oxycodone, oxymorphone, hydromorphone, pentazocine, and methadone, among others, as well as combinations and pharmaceutically acceptable salts, esters and other derivatives of the same.

Examples of non-narcotic analgesic agents for use in the present invention may be selected from suitable members of the following: analgesic agents such as acetaminophen, and non-steroidal anti-inflammatory drugs such as aspirin, diflunisal, salsalate, ibuprofen, ketoprofen, naproxen, indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib, among others, as well as combinations and pharmaceutically acceptable salts, esters and other derivatives of the same.

Examples of local anesthetic agents for use in the present invention may be selected from suitable members of the following: benzocaine, cocaine, lidocaine, mepivacaine, and novacaine, among others, as well as combinations and pharmaceutically acceptable salts, esters and other derivatives of the same.

Examples of anticancer drugs include alkyating agents such as mechlorethamine, nitrosoureas (carmustine, lomustine), melphalan, cyclophosphamide, busulfan and procarbazine, antimetabolites such as methotrexate, 6-thioguanine, 5-fluorouracil, 6-mercaptopurine, cytosine arabinoside, gemcitabine, fludarabine and capecitabine, antimitotics such as vincristine, vinblastine, paclitaxel and docetaxel, hormones such as estrogens, prednisone, goserelin, anti-estrogen (tamoxifen), flutamide, leuprolide, immunosuppressives such as azathioprine, tacrolimus (FK506), cyclosporin a, natural products such as dactinomycin, bleomycin, camptothecin and analogs (e.g., irinotecan and topotecan), daunorubicin, mitomycin C, doxorubicin, etoposide (VP-16), and other agents such as hydroxyurea, asparaginase, amsacrine, cisplatin, carboplatin, mitoxantrone and imatinib.

Many of the above and other urologically beneficial agents may be found, for example, in *The Merck Index*, 14$^{th}$ Edition, M. J. O'Neil, Senior Editor, published by Merck Research Laboratories, 2006.

Urologically beneficial agents may be provided in a liquid composition, for instance, as a solution or dispersion within a suitable liquid, which may comprise water and/or an organic solvent.

In many embodiments, various portions of the medical apparatuses of the disclosure (e.g., pump, reservoir, catheter, urological medical device, and components of the foregoing) are formed at least partially from polymeric materials. Polymeric materials are materials that comprise one or more polymers. Polymers may be selected, for example, from suitable members of the following, among others: polycarboxylic acid polymers and copolymers including polyacrylic acids; acetal polymers and copolymers; acrylate and methacrylate polymers and copolymers (e.g., n-butyl methacrylate); cellulosic polymers and copolymers; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; polycarbonates; polyacrylonitriles; polyvinylpyrrolidones; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropenes) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers; as well as blends and further copolymers of the above.

In certain embodiments, the various portions of the medical apparatuses of the disclosure which are implanted or inserted into the subject (e.g., catheter, urological medical device, and components thereof) may comprise one or more optional imaging agents. For example, x-ray based fluoroscopy is a diagnostic imaging technique that allows real-time patient monitoring of motion within a patient. To be fluoroscopically visible, devices and/or compositions are typically rendered more absorptive of x-rays than the surrounding tissue. In various embodiments, this is accomplished by the use of radio-opaque agents. Examples of radio-opaque agents for use in connection with x-ray fluoroscopy include metals, metal salts and oxides (particularly bismuth salts and oxides), and iodinated compounds, among others. More specific examples of such radio-opaque agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others.

As noted above, the present invention provides medical apparatuses that deliver one or more urologically beneficial agents into the urinary tract of a subject.

In one aspect, the invention provides medical apparatuses in which at least one urologically beneficial agent is delivered from an external reservoir outside to the body, through a lumen of a catheter that extends into the urinary tract, and into a lumen of a urological medical device that is positioned within the urinary tract. Typically, the at least one urologically beneficial agent is delivered to the distal end of the urological medical device, to the lateral surface of the urological medical device, or both.

In certain embodiments (e.g., where the apparatuses are not configured to deliver the urologically beneficial agents by gravity feed), the apparatuses may comprise a pump for pumping the urologically beneficial agents from the reservoir, through the catheter and into the urological medical device. Suitable pumps may be selected from peristaltic pumps, diaphragm-type pumps, piston pumps and rotary gear-type pumps, among others.

The catheter is typically formed from a polymeric material, for example, selected from suitable polymers set forth above. Specific examples include polyurethanes, polyether-block-polyamide copolymers (e.g., Pebax® resins), silicones, and ethylene-vinyl acetate copolymers, among others.

The urological medical device may be formed from a biostable material or a biodisintegrable material. Typically, the urological medical device is formed from a polymeric material, for example, selected from suitable polymers set forth above, including polyesters (e.g., polylactide, polyglycolide, polylactide-co-glycolide, etc.), polyurethanes, polyether-block-polyamide copolymers (e.g., Pebax® resins), silicones, and ethylene-vinyl acetate copolymers, among others. In certain embodiments, the urological medical device is provided with a retention element (e.g., an element which can be changed in shape once positioned in the kidney or bladder, for instance, a coil, balloon, etc.).

The connection between the catheter lumen and the urological medical device lumen may be made, for example, by abutting the catheter and the urological medical device, by inserting the end of the catheter into a urological medical device lumen, by inserting the end of the urological medical device into a catheter lumen, and so forth. The connection may be held in place by friction, by solvent bonding, by heat bonding, using a suitable adhesive, and so forth.

One preferred example of a urological medical device that can be employed with the catheter is a ureteral stent. One example of a stent design is a modified double pigtail Percuflex® Ureteral Stent, for example, a Polaris™ Dual Durometer Percuflex® Ureteral Stent with HydroPlus™ Coating, available from Boston Scientific, Natick, Mass., USA. Stents of this type employ an extrusion to combine a firm durometer ethylene vinyl acetate copolymer (EVA) at the distal (renal) end, which improves stent advancement, and a soft durometer EVA at the proximal (bladder) end, which improves comfort. Such stents contain a urine carrying lumen for carrying urine from the kidney to the bladder. Such stents may be modified in various ways as discussed below.

In addition to a urine carrying lumen, ureteral stents in accordance with the present disclosure may be provided with at least one agent delivery lumen that extends into the stent from the proximal (bladder) end of the stent in the direction of the kidney.

In some embodiments, the at least one agent delivery lumen extends the entire length (or nearly the entire length) of the stent, allowing delivery of a urologically beneficial agent to the kidney.

In some embodiments, the at least one agent delivery lumen extends only from the proximal (bladder) end of the stent into the ureter section of the stent (not to the kidney portion of the stent), allowing delivery of a urologically beneficial agent to the ureter.

In some embodiments, the at least one agent delivery lumen may be provided with one or more exit apertures (e.g., holes, slots, pores, etc.) along its length for the delivery of a urologically beneficial agent into the ureter through the side (lateral) surface of the stent.

In some embodiments, such apertures are blocked by a biodisintegrable blocking material (e.g., comprising a biodegradable polymer, a biodissolvable polymer, a biodissolvable small molecule such as sugar or salt, etc.) For example, such an embodiment may allow at least one urologically beneficial agent to be initially delivered entirely to the kidney (i.e., through the main agent delivery lumen), followed by delivery to selected portions of the ureter upon biodisintegration of the biodisintegrable blocking material (i.e., through the exit apertures).

Typically, the biodisintegrable blocking material is one that undergoes significant (i.e., at least 50 wt % up to and including total disappearance) disintegration (e.g., due to dissolution, degradation, etc.) within 7 days, within 5 days, within 3 days or even within 1 day or less.

Exit apertures can be placed, for example, to selectively provide drug to any of the following ureteral areas: (a) the lower, middle and upper ureter, (b) the lower and middle ureter, but not the upper ureter, (c) the middle and upper ureter, but not the lower ureter, (d) the lower and upper ureter, but not the middle ureter, (e) the upper ureter, but not the lower and middle ureter, (f) the lower ureter, but not the upper and middle ureter, and (g) the middle ureter, but not the lower and upper ureter. As used herein, "lower ureter" is the lower 25-50% of the length of the ureter (bladder end), "upper ureter" is the upper 25-50% of the length of the ureter (kidney end), and "middle ureter" is the middle 25-50% of the length of the ureter.

Turning now to FIGS. 3A-3B, a schematic illustration of a medical apparatus 100 is shown in accordance with an embodiment of the invention, which includes a reservoir 114, pump 112, a catheter 116 and a stent 110.

The stent 110 is provided with an agent delivery lumen 110a and a urine carrying lumen 110b, which extend the entire length of the device. The stent 110 is further provided with apertures 110c connecting the agent delivery lumen 110a with an exterior (i.e., lateral surface) of the device. FIG. 3B is a cross-sectional view of the ureteral stent of FIG. 3A, taken along plane B-B and illustrates the connection that the aperture 110c provides between the agent delivery lumen 110a and the exterior of the device.

FIG. 3C is an alternative to cross-section FIG. 3B, which shows the aperture blocked by a biodisintegrable blocking material 112.

FIG. 3D is an alternative to cross-section FIG. 3B, which shows multiple apertures 110c between the agent delivery lumen 110a and the exterior of the device at a given axial position (i.e., the axial position of plane B-B).

Also shown in FIG. 3A is a reservoir 114 from which a urologically beneficial agent is drawn via a tube 118 into a pump 112. The urologically beneficial agent is then forced from pump 112 into a catheter 116. The urologically beneficial agent then travels through the catheter 116 and enters agent delivery lumen 110a at the proximal (bladder) end 110p of the stent 110. The urologically beneficial agent flows through the stent 110 and out of the agent delivery lumen 110a at the distal (kidney) end 110d of the stent 110. The urologically beneficial agent also flows through the apertures 110c, either at the point in time that the agent reaches the apertures (where the apertures are not blocked) or upon disintegration of a biodisintegrable blocking material (where the apertures are initially blocked by the biodisintegrable blocking material).

In some embodiments, a ureteral stent is provided which contains a first agent delivery lumen that extends through the stent to the kidney for delivery of a first urologically beneficial agent to the kidney, and a second agent delivery lumen that extends into the stent and has one or more apertures (which may or may not be provided with a biodisintegrable blocking material) for delivering a second urologically beneficial agent to the ureter. For example, the first urologically beneficial agent may be a pain killer (e.g., ketorolac, etc.) and the second urologically beneficial agent may be an antimicrobial agent (e.g., triclosan, etc.).

Figure 4A:
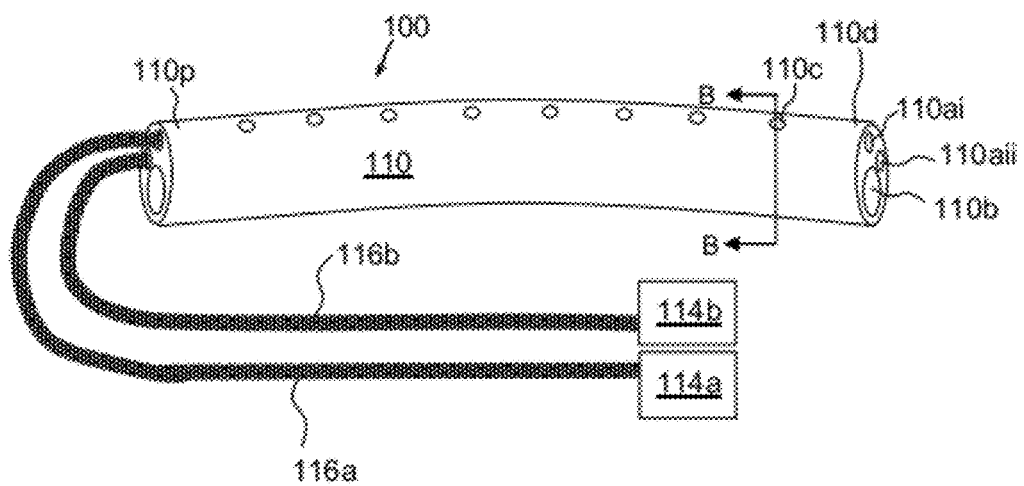
FIG. 4A is a schematic illustration of a medical device in accordance with an embodiment of the invention.
Figure 4B:
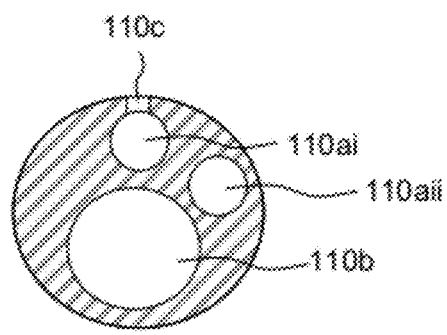
FIG. 4B is a cross-section of the medical device of FIG. 4A, taken along plane B-B.

Turning now to FIGS. 4A-4B, a schematic illustration of a medical apparatus 100 is shown in accordance with an embodiment of the invention. The apparatus includes a stent 110, which is provided with a first agent delivery lumen 110ai, a second agent delivery lumen 110aii, and a urine carrying lumen 110b, each of which extends the length of the device. The stent 110 is further provided with apertures 110c connecting the first agent delivery lumen 110ai with the exterior of the device (i.e., the lateral surface of the stent 110). FIG. 4B is a cross-sectional view of the ureteral stent of FIG. 4A, taken along plane B-B and illustrates the fluid connection that the apertures 110c provide with the exterior of the device. (In an alternative embodiment, the aperture 110c may be blocked by a biodisintegrable blocking material, or multiple apertures can be provided at a given axial position, as described above.)

Also shown in FIG. 4A is a first reservoir 114a from which a first urologically beneficial agent is pumped into a first catheter 116a. The first urologically beneficial agent travels through the first catheter 116a and enters first agent delivery lumen 110ai at the proximal end 110p of the stent 110. The first urologically beneficial agent flows through the stent 110 and out of the first agent delivery lumen 110ai at the distal end 110d of the stent 110. The first urologically beneficial agent also flows through the apertures 110c. A second urologically beneficial agent is pumped from a second reservoir 114b into a second catheter 116b. The second urologically beneficial agent travels through the second catheter 116a and enters second agent delivery lumen 110aii at the proximal end 110p of the stent 110. The second urologically beneficial agent flows through the stent 110 and out of the second agent delivery lumen 110aii at the distal end 110d of the stent.

Although two separate catheters 116a, 116b are shown in FIGS. 4A-4B, in other embodiments, a single catheter may be provided which contains first and second catheter lumens for independently transporting the first and second urologically beneficial agents.

Figure 6A:
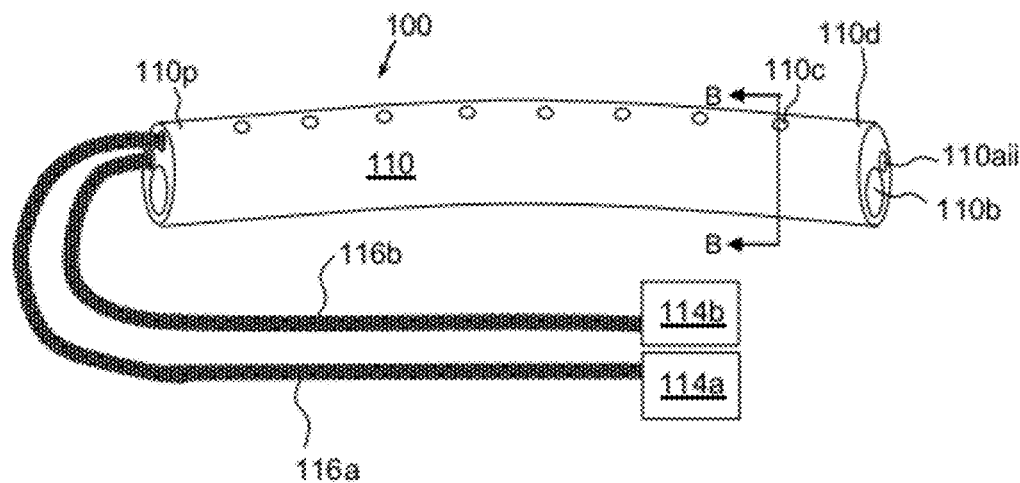
FIG. 6A is a schematic illustration of a medical device in accordance with an embodiment of the invention.
Figure 6B:
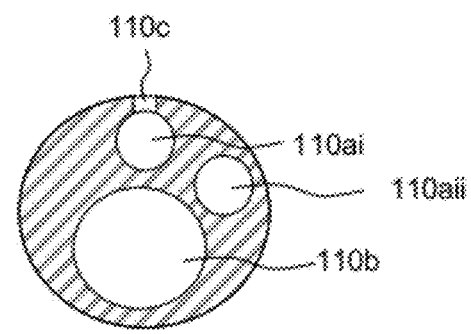
FIG. 6B is a cross-section of the medical device of FIG. 6A, taken along plane B-B.

FIGS. 6A-6B show a device like that shown in FIGS. 4A-4B, with the exception that, in the device of FIGS. 6A-6B, the first lumen 110ai does not extend all the way the to the distal end 110d of the stent 110. Consequently, the first urologically beneficial agent flows from the first lumen 110ai through apertures 110c on the lateral surface of the stent 110 (see FIG. 6B); however, the first urologically beneficial agent does not flow to the distal end 110d of the stent 110 as it does in FIGS. 4A-4B.

In other embodiments, a ureteral stent is provided which comprises (a) a lumen that extends from the proximal (bladder) end of the stent to the ureter or kidney (with or without apertures) for delivery of a first urologically beneficial agent (e.g., a pain killer) and (b) a reservoir which is connected to the exterior of the device via one or more apertures and which is loaded with a second urologically beneficial agent (e.g., a hyaluronic acid solution to prevent urinary tract infection).

Figure 5A:
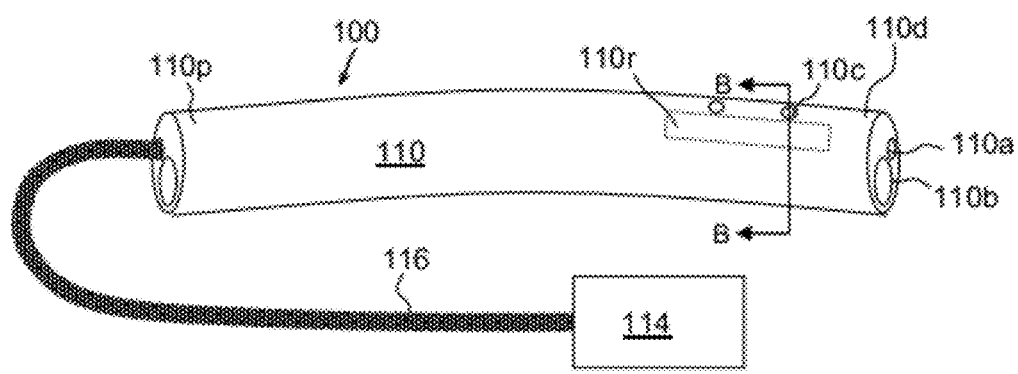
FIG. 5A is a schematic illustration of a medical device in accordance with an embodiment of the invention.
Figure 5B:
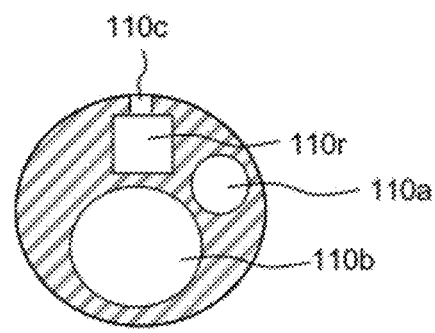
FIG. 5B is a cross-section of the medical device of FIG. 5A, taken along plane B-B.

Turning now to FIG. 5A-5B, a schematic illustration of a medical apparatus 100 is shown in accordance with an embodiment of the invention. The stent 110 is provided with agent delivery lumen 110a and a urine carrying lumen 110b, which extend the entire length of the device. The stent 110 is further provided with apertures 110c connecting an internal reservoir 110r (shown with hidden lines in FIG. 5A) with the exterior of the device. FIG. 5B is a cross-sectional view of the ureteral stent of FIG. 5A, taken along plane B-B and illustrates the reservoir 110r, which carries a second urologically beneficial agent, and the connection that the apertures 110c provide between the internal reservoir 110r and the exterior of the device. The second urologically beneficial agent flows from the internal reservoir 110r through the apertures 110c, either immediately upon placement of the stent in the body (in the case where the apertures are not blocked as shown) or upon disintegration of a biodisintegrable blocking material (where the apertures are initially blocked by the biodisintegrable blocking material).

Also shown in FIG. 5A is an external reservoir 114 from which a first urologically beneficial agent is pumped into a catheter 116. The first urologically beneficial agent travels through the catheter 116 and enters the agent delivery lumen 110a at the proximal end of the stent 110. The first urologically beneficial agent flows through the stent 110 and out of the agent delivery lumen 110a at the distal end of the stent.

Various aspects of the invention of the invention relating to the above are enumerated in the following paragraphs:

Aspect 1. A medical apparatus comprising: (a) a first external reservoir that is configured to remain external to a urinary tract of a patient; (b) a first catheter having proximal and distal ends that is configured to be inserted into the urinary tract, the catheter having a first catheter lumen that extends from the proximal end to the distal end of the first catheter; and (c) a urological medical device having proximal and distal ends that is configured to be implanted in the urinary tract, the urological medical device having a first agent delivery lumen that extends from the proximal end of the urological medical device into the urological medical device; wherein an interior of the first external reservoir is in fluid communication with the proximal end of the first catheter lumen, wherein the distal end of the first catheter lumen is in fluid communication with the proximal end of the first agent delivery lumen, and wherein the medical apparatus is adapted to deliver a first urologically beneficial agent from the interior of the first external reservoir, through the first catheter lumen, and into the first agent delivery lumen.

Aspect 2. The medical apparatus of aspect 1, wherein the apparatus further comprises a pump for delivering the urologically beneficial agent from the interior of the first external reservoir, through the catheter lumen, and into the first agent delivery lumen.

Aspect 3. The medical apparatus of aspect 1, wherein the urological medical device is a ureteral stent having a proximal end, a distal end and a lateral surface.

Aspect 4. The medical apparatus of aspect 3, wherein the ureteral stent comprises a kidney retention element.

Aspect 5. The medical apparatus of aspect 3, wherein the first agent delivery lumen extends from the proximal end to the distal end of the ureteral stent.

Aspect 6. The medical apparatus of aspect 3, wherein the ureteral stent is provided with one or more apertures that provide fluid communication between the first urological medical device lumen and the lateral surface of the ureteral stent.

Aspect 7. The medical apparatus of aspect 6, wherein the apertures are blocked by a biodisintegrable blocking material.

Aspect 8. The medical apparatus of aspect 6, wherein the first agent delivery lumen extends to the distal end of the ureteral stent.

Aspect 9. The medical apparatus of aspect 6, wherein the first agent delivery lumen does not extend to the distal end of the ureteral stent.

Aspect 10. The medical apparatus of aspect 3, wherein the ureteral stent comprises a second agent delivery lumen that extends from the proximal end of the ureteral stent into the ureteral stent.

Aspect 11. The medical apparatus of aspect 10, further comprising a second external reservoir that is configured to remain external to a urinary tract of a patient and a second catheter lumen, wherein the medical apparatus is adapted to deliver a second urologically beneficial agent from the interior of the second reservoir, through the second catheter lumen, and into the second agent delivery lumen.

Aspect 12. The medical apparatus of aspect 11, wherein the first catheter comprises the second catheter lumen.

Aspect 13. The medical apparatus of aspect 11, further comprising a second catheter that comprises the second catheter lumen.

Aspect 14. The medical apparatus of aspect 10, wherein the second agent delivery lumen extends to the distal end of the stent.

Aspect 15. The medical apparatus of aspect 10, wherein the second agent delivery lumen does not extend to the distal end of the stent.

Aspect 16. The medical apparatus of aspect 10, wherein the ureteral stent is provided with one or more apertures that provide fluid communication between the second urological medical device lumen and a lateral surface of the device.

Aspect 17. The medical apparatus of aspect 16, wherein the second agent delivery lumen does not extend to the distal end of the stent.

Aspect 18. The medical apparatus of aspect 17, wherein the first agent delivery lumen extends to the distal end of the ureteral stent.

Aspect 19. The medical apparatus of aspect 3, further comprising an internal reservoir in the ureteral stent and one or more apertures that provide fluid communication between the internal reservoir and a lateral surface of the device.

Aspect 20. The medical apparatus of aspect 19, wherein the first agent delivery lumen extends to the distal end of the ureteral stent.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A medical apparatus comprising: (a) a first external reservoir that is configured to remain external to a urinary tract of a patient; (b) a first catheter having proximal and distal ends that is configured to be inserted into the urinary tract, the catheter having a first catheter lumen that extends from the proximal end to the distal end of the first catheter; (c) a urological medical device having proximal and distal ends that is configured to be implanted in the urinary tract, the urological medical device having a first agent delivery lumen that extends from the proximal end of the urological medical device into the urological medical device; wherein an interior of the first external reservoir is in fluid communication with the proximal end of the first catheter lumen, wherein the distal end of the first catheter lumen is in fluid communication with the proximal end of the first agent delivery lumen, and wherein the medical apparatus is adapted to deliver a first urologically beneficial agent from the interior of the first external reservoir, through the first catheter lumen, and into the first agent delivery lumen, and (d) a pump for delivering the urologically beneficial agent from the interior of the first external reservoir, through the catheter lumen, and into the first agent delivery lumen.

2. The medical apparatus of claim 1, wherein the urological medical device is a ureteral stent having a proximal end, a distal end and a lateral surface.

3. The medical apparatus of claim 2, wherein the ureteral stent comprises a kidney retention element.

4. The medical apparatus of claim 2, wherein the first agent delivery lumen extends from the proximal end to the distal end of the ureteral stent.

5. The medical apparatus of claim 2, wherein the ureteral stent is provided with one or more apertures that provide fluid communication between the first urological medical device lumen and the lateral surface of the ureteral stent.

6. A medical apparatus comprising: (a) a first external reservoir that is configured to remain external to a urinary tract of a patient; (b) a first catheter having proximal and distal ends that is configured to be inserted into the urinary tract, the catheter having a first catheter lumen that extends from the proximal end to the distal end of the first catheter; and (c) a urological medical device having proximal and distal ends that is configured to be implanted in the urinary tract, the urological medical device having a first agent delivery lumen that extends from the proximal end of the urological medical device into the urological medical device; wherein an interior of the first external reservoir is in fluid communication with the proximal end of the first catheter lumen, wherein the distal end of the first catheter lumen is in fluid communication with the proximal end of the first agent delivery lumen, wherein the medical apparatus is adapted to deliver a first urologically beneficial agent from the interior of the first external reservoir, through the first catheter lumen, and into the first agent delivery lumen, wherein the urological medical device is a ureteral stent having a proximal end, a distal end and a lateral surface, wherein the ureteral stent is provided with one or more apertures that provide fluid communication between the first urological medical device lumen and the lateral surface of the ureteral stent, and wherein the apertures are blocked by a biodisintegrable blocking material.

7. The medical apparatus of claim 5, wherein the first agent delivery lumen extends to the distal end of the ureteral stent.

8. The medical apparatus of claim 5, wherein the first agent delivery lumen does not extend to the distal end of the ureteral stent.

9. The medical apparatus of claim 2, wherein the ureteral stent comprises a second agent delivery lumen that extends from the proximal end of the ureteral stent into the ureteral stent.

10. The medical apparatus of claim 9, further comprising a second external reservoir that is configured to remain external to a urinary tract of a patient and a second catheter lumen, wherein the medical apparatus is adapted to deliver a second urologically beneficial agent from the interior of the second reservoir, through the second catheter lumen, and into the second agent delivery lumen.

11. The medical apparatus of claim 10, wherein the first catheter comprises the second catheter lumen.

12. The medical apparatus of claim 10, further comprising a second catheter that comprises the second catheter lumen.

13. The medical apparatus of claim 9, wherein the second agent delivery lumen extends to the distal end of the stent.

14. The medical apparatus of claim 9, wherein the second agent delivery lumen does not extend to the distal end of the stent.

15. The medical apparatus of claim 9, wherein the ureteral stent is provided with one or more apertures that provide fluid communication between the second urological medical device lumen and a lateral surface of the device.

16. The medical apparatus of claim 15, wherein the second agent delivery lumen does not extend to the distal end of the stent.

17. The medical apparatus of claim 16, wherein the first agent delivery lumen extends to the distal end of the ureteral stent.

18. A medical apparatus comprising: (a) a first external reservoir that is configured to remain external to a urinary tract of a patient; (b) a first catheter having proximal and distal ends that is configured to be inserted into the urinary tract, the catheter having a first catheter lumen that extends from the proximal end to the distal end of the first catheter; and (c) a urological medical device having proximal and distal ends that is configured to be implanted in the urinary tract, the urological medical device having a first agent delivery lumen that extends from the proximal end of the urological medical device into the urological medical device; wherein an interior of the first external reservoir is in fluid communication with the proximal end of the first catheter lumen, wherein the distal end of the first catheter lumen is in fluid communication with the proximal end of the first agent delivery lumen, wherein the medical apparatus is adapted to deliver a first urologically beneficial agent from the interior of the first external reservoir, through the first catheter lumen, and into the first agent delivery lumen, wherein the urological medical device is a ureteral stent having a proximal end, a distal end and a lateral surface, and wherein the ureteral stent comprises an internal reservoir and one or more apertures that provide fluid communication between the internal reservoir and a lateral surface of the device.

19. The medical apparatus of claim 18, wherein the first agent delivery lumen extends to the distal end of the ureteral stent.

* * * * *